(12) United States Patent
Egley et al.

(10) Patent No.: US 11,577,013 B2
(45) Date of Patent: Feb. 14, 2023

(54) IN-LINE HEATING OF DIALYSIS FLUIDS

(71) Applicant: Fresenius Medical Care Holdings, Inc., Waltham, MA (US)

(72) Inventors: Bert D. Egley, Walnut Creek, CA (US); Jon F. Moss, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 800 days.

(21) Appl. No.: 16/565,653

(22) Filed: Sep. 10, 2019

(65) Prior Publication Data

US 2021/0069399 A1    Mar. 11, 2021

(51) Int. Cl.
*A61M 1/16*     (2006.01)
*A61M 1/36*     (2006.01)

(52) U.S. Cl.
CPC ............ *A61M 1/166* (2014.02); *A61M 1/367* (2013.01); *A61M 2205/127* (2013.01)

(58) Field of Classification Search
CPC .................. A61M 1/166; A61M 1/367; A61M 2205/127; A61M 2205/36; A61M 2206/11; A61M 2206/14; A61M 1/1664; A61M 1/28
See application file for complete search history.

(56) References Cited

U.S. PATENT DOCUMENTS

| | | | |
|---|---|---|---|
| 6,595,948 B2 | 7/2003 | Suzuki et al. | |
| 6,743,201 B1 * | 6/2004 | Donig | A61M 1/166 165/169 |
| 6,764,761 B2 | 7/2004 | Eu et al. | |
| 6,869,538 B2 | 3/2005 | Yu et al. | |
| 7,153,285 B2 | 12/2006 | Lauman et al. | |
| 7,153,286 B2 | 12/2006 | Busby et al. | |
| 7,809,254 B2 | 10/2010 | Lindsay et al. | |
| 8,038,639 B2 | 10/2011 | Lo et al. | |
| 8,419,933 B2 | 4/2013 | Rohde et al. | |
| 9,358,331 B2 | 6/2016 | Fulkerson et al. | |
| 10,076,599 B2 | 9/2018 | Eyrard et al. | |
| 2008/0031773 A1 * | 2/2008 | Eccleston | A61M 1/3666 604/4.01 |
| 2009/0012450 A1 | 1/2009 | Shah et al. | |
| 2011/0192796 A1 | 8/2011 | Smejtek et al. | |
| 2014/0046248 A1 | 2/2014 | Fini et al. | |
| 2019/0076590 A1 | 3/2019 | Plahey et al. | |

OTHER PUBLICATIONS

International Search Report and Written Opinion for International application No. PCT/US2020/046059, dated Jan. 22, 2021, 18 pages.

* cited by examiner

*Primary Examiner* — Krishnan S Menon
(74) *Attorney, Agent, or Firm* — KDB Firm PLLC

(57) ABSTRACT

Dialysis systems and methods for operating dialysis machines (e.g., peritoneal dialysis machines) for conducting dialysis treatments are disclosed. The dialysis system may include a dialysis machine for transferring dialysate to a patient from a dialysate source. The dialysate may flow from the dialysate source through a cartridge or cassette (e.g., a disposable cartridge or cassette) positionable within the dialysis machine. The cassette includes a fluid flow channel. The dialysis machine includes a heating chamber for in-line heating of the dialysate in the fluid flow channel. The fluid flow channel is arranged and configured to provide turbulent flow of the dialysate through the fluid flow channel to provide increased heat transfer from the heating chamber to the dialysate.

20 Claims, 14 Drawing Sheets

IN-LINE HEATING OF DIALYSIS FLUIDS

FIELD OF THE DISCLOSURE

The disclosure generally relates to dialysis machines, and more particularly to in-line heating of fluids, especially dialysis fluid in dialysis systems and methods.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated PD machines, called PD cyclers, are designed to control the entire PD process so that it can be performed at home, usually overnight, without clinical staff in attendance.

A dialysis machine, such as a PD machine, may include one or more containers (e.g., bags) containing a fluid (e.g., a dialysate) for patient infusion. In PD machines, for example, tubing as fluid lines are inserted into an abdomen of a patient for flowing fresh dialysate and removing used dialysate, waste, and excess fluid. In bags containing fresh dialysate, the dialysis needs to be heated to body temperature prior to being inserted into the patient.

Methods for heating dialysate include batch and in-line heating, With batch heating, a dialysis machine, such as, for example, a PD machine, may incorporate a heater tray positioned on, for example, the top of the dialysis machine. The heater tray may be sized and shaped to accommodate a heater bag of dialysate (e.g., a 5 L bag of dialysate) for batch heating. The heater tray includes a heating element for heating the dialysate prior to delivery into the patient. In use, dialysate bags may be suspended from hooks on the sides of a cart containing the dialysis machine. The heater bag may be positioned on the heater tray. Dialysate from the dialysate bags may be transferred to the heater bag in batches. For example, a batch of dialysate may be transferred from one or more of the dialysate bags to the heater bag, where the dialysate is heated by the heating element. When the batch of dialysate has reached a predetermined temperature (e.g., approximately 98°-100° F., 37° C.), the batch of dialysate may be flowed into the patient.

With in-line heating, a dialysis machine, such as, for example, a PD machine, may incorporate a heating chamber including one or more heating elements. During use, dialysate from one or more dialysate bags may be transferred directly to the patient through the heating chamber. The dialysate bags may be connected to a cassette, which may be insertable into the PD machine, typically into the heating chamber of the dialysis machine. The dialysate bags may be connected to the cassette via dialysate bag lines and the dialysate bag lines may be used to pass dialysate from dialysate bags to the cassette during use. That is, for example, a heating chamber may be disposed internal to the PD machine. The cassette may be insertable into an opening or cavity formed in the PD machine. The cassette may be configured so that dialysate may continually flow through the cassette, which may be surrounded by the heating chamber to achieve a predetermined temperature before flowing into the patient. For example, in one embodiment, one or more internal heating elements may be positioned above and/or below the opening or cavity, so that when the cassette is inserted into the opening or cavity formed in the PD machine, the one or more heating elements affect the temperature of the dialysate flowing through the cassette. Alternatively, in some embodiments, the heating chamber may be configured so that a portion of tubing in the system may be passed by, around, or otherwise configured with respect to, the one or more heating elements. Thus, in use, the dialysate continuously flows through the cassette "in-line" with the dialysis machine, reaching an acceptable temperature by the application of internal heating elements.

As described above, embodiments of PD machines incorporating in-line heaters may be susceptible to temperature variation of the dialysate. Thus, there is a need in dialysis to deliver dialysate accurately at specific temperatures, for example, at 37 degrees Celsius (e.g., body temperature). Additionally, it is desirable to heat the dialysate to the specified temperature as quickly as possible. By heating the dialysate to the specified temperature in a shorter period of time, the total treatment time can be reduced resulting in greater efficacies and reduced expense. Moreover, it would be advantageous to minimize the size of the cassette needed to heat the dialysate.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment is disclosed. The dialysis system comprises a dialysis machine for transferring dialysate to a patient from a dialysate source, the dialysis machine including a cavity and a heating chamber to heat the dialysate to a predetermined temperature; and a disposable cassette positionable within the cavity, the cassette being in fluid communication with the patient and the dialysate source, the cassette including a fluid flow channel; wherein the fluid flow channel is arranged and configured to provide turbulent flow of dialysate through the fluid flow channel to provide increased heat transfer from the heating chamber to the dialysate.

In this and other embodiments, the fluid flow channel is arranged and configured to achieve a Reynold's Number (Nr) of 4,000 or greater.

In this and other embodiments, the fluid flow channel is arranged and configured with a cross-sectional area of between 1.0 mm$^2$ and 2.1 mm$^2$.

In this and other embodiments, the fluid flow channel has a width of approximately 2 mm and a height of approximately 1 mm.

In this and other embodiments, the fluid flow channel includes a plurality of projections extending from an inner surface thereof, the plurality of projections protruding into a path of the dialysate.

In this and other embodiments, the cassette further comprises a header coupled to the fluid flow channel, the header subdividing a first pathway of the fluid flow channel into a plurality of downstream, parallel fluid flow pathways.

In this and other embodiments, the fluid flow channel includes a first stage and a second stage, the first stage of the fluid flow channel being arranged and configured to provide turbulent flow of dialysate through the first stage of the fluid flow channel to provide increased heat transfer from the heating chamber to the dialysate, the second stage of the fluid flow channel being arranged and configured to provide laminar flow of dialysate through the second stage of the fluid flow channel.

In this and other embodiments, the second stage of the fluid flow channel is in series with the first stage of the fluid flow channel.

In this and other embodiments, the fluid flow channel includes an inlet and an outlet, the first stage of the fluid flow channel being positioned in series between the inlet and the second stage of the fluid flow channel, the second stage of the fluid flow channel being positioned in series between the first stage of the fluid flow channel and the outlet.

In this and other embodiments, the heating chamber includes first and second heating elements for heating the first and second stages of fluid flow channel, respectively.

In this and other embodiments, the a thermal gel pouch is positioned between a heating element of the heating chamber and the cassette, the pouch being in direct contact with the heating element and the cassette.

According to an exemplary embodiment of the present disclosure, a disposable cassette is disclosed. The disposable cassette being positionable within a cavity of a dialysis machine that includes a heating chamber, the cassette being in fluid communication with a patient and a dialysate source for transferring dialysate therebetween. The disposable cassette comprises a fluid flow channel arranged and configured to provide turbulent flow of dialysate through the fluid flow channel to provide increased heat transfer from the heating chamber to the dialysate.

In this and other embodiments, the fluid flow channel is arranged and configured to achieve a Reynold's Number (Nr) of 4,000 or greater.

In this and other embodiments, the fluid flow channel is arranged and configured with a cross-sectional area of between 1.0 mm$^2$ and 2.1 mm$^2$.

In this and other embodiments, the fluid flow channel has a width of approximately 2 mm and a height of approximately 1 mm.

In this and other embodiments, the fluid flow channel includes a plurality of projections extending from an inner surface thereof, the plurality of projections protruding into a path of the dialysate.

In this and other embodiments, the cassette further comprises a header coupled to the fluid flow channel, the header subdividing a first pathway of the fluid flow channel into a plurality of downstream, parallel fluid flow pathways.

In this and other embodiments, the fluid flow channel includes a first stage and a second stage, the first stage of the fluid flow channel being arranged and configured to provide turbulent flow of dialysate through the first stage of the fluid flow channel to provide increased heat transfer from the heating chamber to the dialysate, the second stage of the fluid flow channel being arranged and configured to provide laminar flow of dialysate through the second stage of the fluid flow channel.

In this and other embodiments, the second stage of the fluid flow channel is in series with the first stage of the fluid flow channel.

In this and other embodiments, the fluid flow channel includes an inlet and an outlet, the first stage of the fluid flow channel being positioned in series between the inlet and the second stage of the fluid flow channel, the second stage of the fluid flow channel being positioned in series between the first stage of the fluid flow channel and the outlet.

According to an exemplary embodiment of the present disclosure, a dialysis system for conducting a dialysis treatment is disclosed. The dialysis system comprises a dialysis machine for transferring dialysate to a patient from a dialysate source, the dialysis machine including a cavity and a heating chamber to heat the dialysate to a predetermined temperature; and a disposable cassette positionable within the cavity, the cassette being in fluid communication with the patient and the dialysate source, the cassette including a fluid flow channel; wherein the heating chamber includes one or more pouches positioned between a heating element of the heating chamber and the cassette, the one or more pouches being in contact with the heating element and the cassette to provide for improved heat distribution from the heating element to the dialysate.

In this and other embodiments, the one or more pouches are thermal gel pouches.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
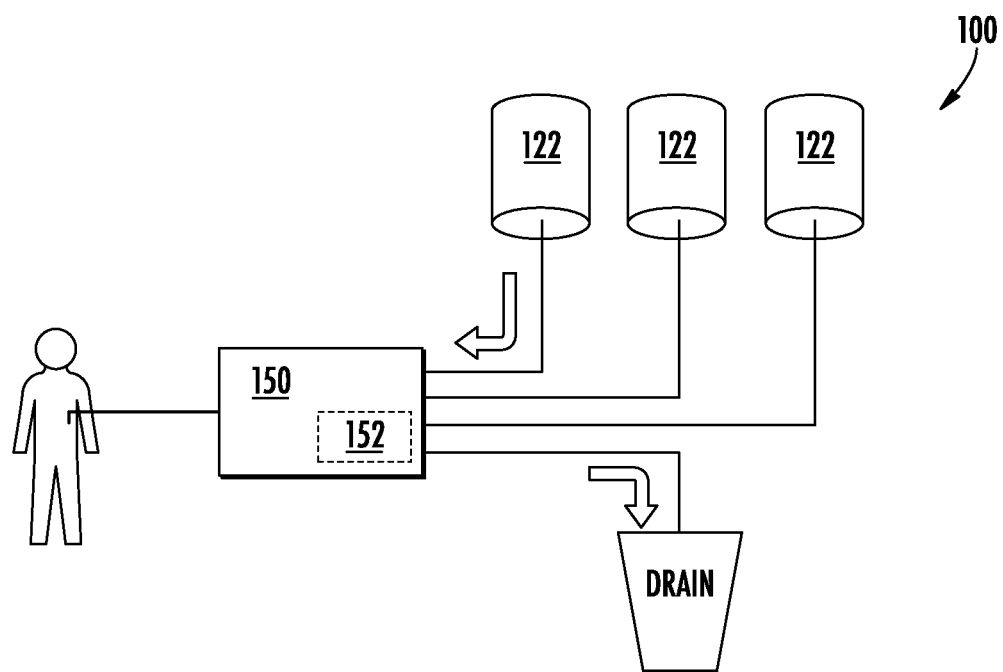
FIG. 1 illustrates an example of an embodiment of a dialysis system.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of improved cassettes arranged and configured to provide improved heat transfer from a heating chamber of a dialysis machine to the dialysate flowed therethrough, will now be described herein.

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are hung near the PD machine 150 which may improve air content management as any air content is disposed by gravity to a top portion of the dialysate bag 122. Valves may be attached to a bottom portion of the dialysate bags 122 so fluid is drawn out and air content delivery is minimized. In one embodiment, as shown, dialysate from the dialysate bags 122 may be transferred directly to the patient through a warmer pouch, a heating chamber, or the like 152 (used interchangeably without the intent to limit) formed in the dialysis machine 150. When the dialysate has reached a predetermined temperature (e.g., approximately 98°-100° F., 37° C.) in the heating chamber 152, the dialysate may be flowed into the patient. As will be described and illustrated in greater detail below, the dialysate bags 122 may be connected to a cartridge or cassette (used interchangeably without the intent to limit), which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected to the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD cycler from a dialysate concentrate, see, e.g., U.S. Pat. No. 10,076,599 to Eyrard et al., entitled "Dry Peritoneal Dialysis Concentrate System," which is incorporated by reference herein in its entirety.

Figure 2:
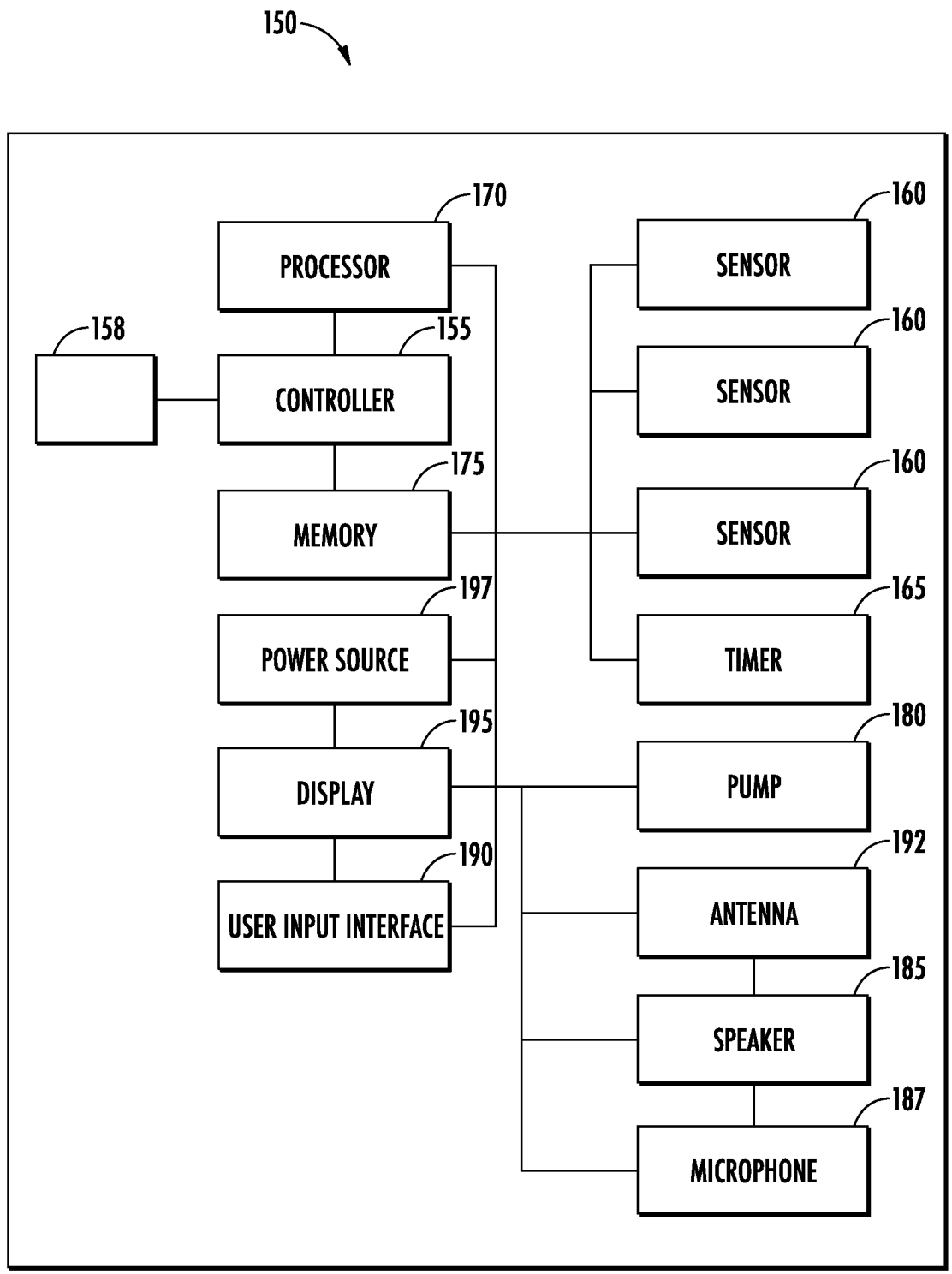
FIG. 2 is a block diagram illustrating an example of an embodiment of a dialysis machine and a controller.

Referring to FIG. 2, a schematic of an exemplary embodiment of a dialysis machine such as, for example, dialysis machine 150 and a controller 155 in accordance with the present disclosure are shown. The machine 150 may be a home dialysis machine, e.g., a PD machine, for performing a dialysis treatment on a patient, and may be included in the system 100 described above with respect to FIG. 1. The controller 155 may automatically control execution of a treatment function during a course of dialysis treatment. The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing triggering of the sensors 160.

In some embodiments, the machine 150 may also include a processor 170, and memory 175, the controller 155, the processor 170, and/or the memory 175, or combinations thereof of the machine 150, may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the heating chamber 152. The controller 155 may also be operatively connected to a speaker 185 and a microphone 187 disposed in the machine 150. A user input interface 190 may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 150 may also be wirelessly connectable via an antenna 192 for remote communication. The machine 150 may also include a display 195 and a power source 197.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 150 or may be coupled to the machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3:
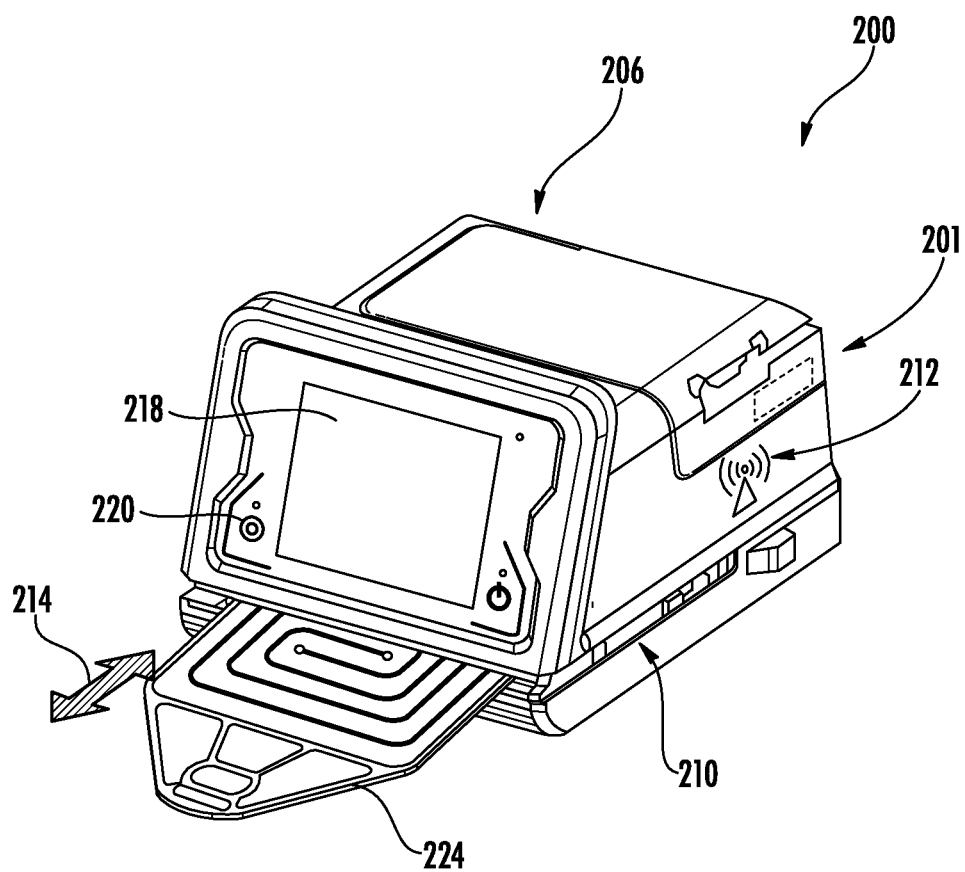
FIGS. 3 and 4 illustrate an example of an embodiment of a dialysis machine that can be used in the dialysis system of FIG. 1.
Figure 4:
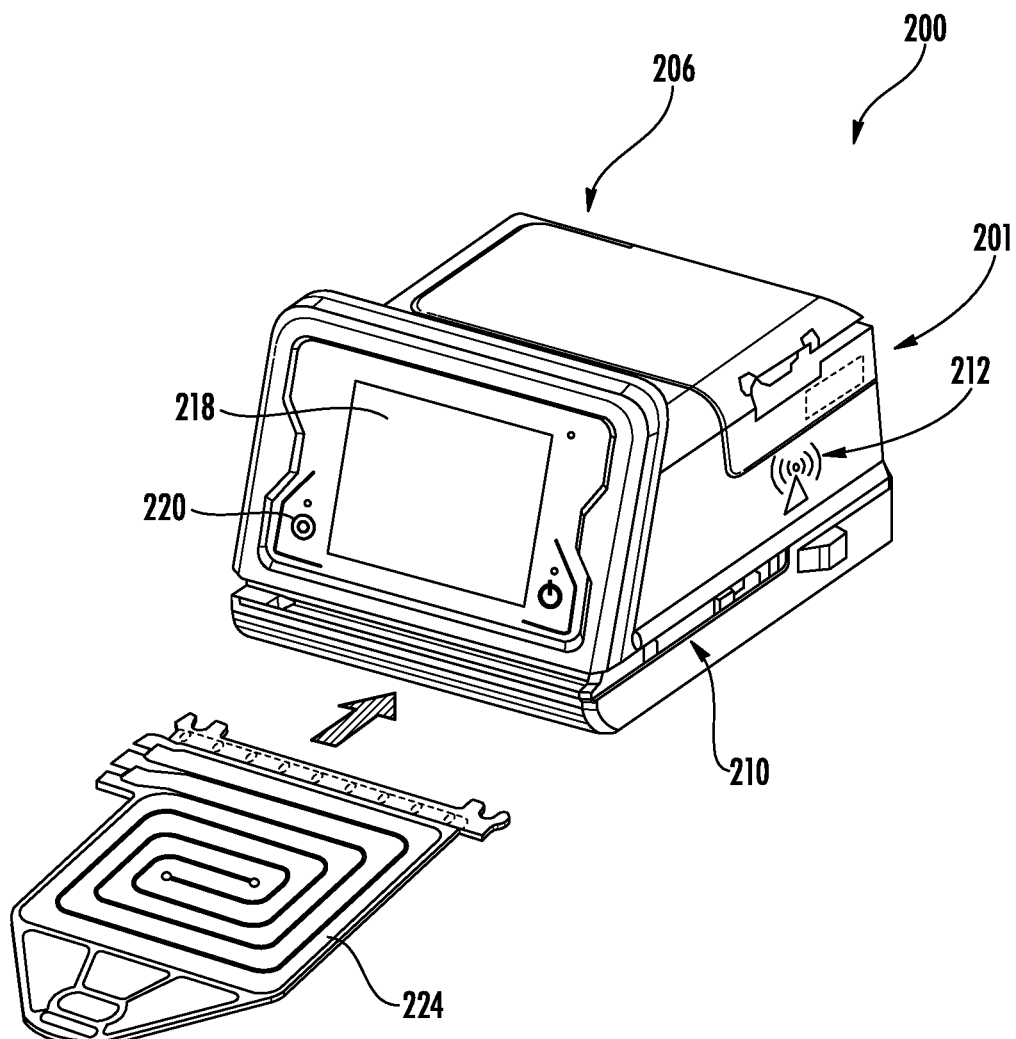

FIGS. 3 and 4 illustrate an example of an embodiment of a dialysis machine 200 such as, for example, dialysis machine 150, that can be used in connection with the dialysis system 100 shown in FIG. 1. The dialysis machine 200 may be implemented in the dialysis system 100 and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment.

The touch screen 218 and the control panel 220 may allow a user to input various treatment parameters to the dialysis machine 200 and to otherwise control the dialysis machine 200. In addition, the touch screen 218 may serve as a display. The touch screen 218 may function to provide information to the patient and the operator of the dialysis system 100. For example, the touch screen 218 may display information related to a dialysis treatment to be applied to the patient, including information related to a prescription.

The dialysis machine 200 may include a processing module 201 that resides inside the dialysis machine 200, the processing module 201 being configured to communicate with the touch screen 218 and the control panel 220. The processing module 201 may be configured to receive data from the touch screen 218, the control panel 220, and sensors, e.g., air, temperature and pressure sensors, and control the dialysis machine 200 based on the received data. For example, the processing module 201 may adjust the operating parameters of the dialysis machine 200. In some embodiments, the processing module 201 may be an MPC823 PowerPC device manufactured by Motorola, Inc.

The dialysis machine 200 may be configured to connect to a network. The connection to network may be via a wired and/or wireless connection. The dialysis machine 200 may include a connection component 212 configured to facilitate the connection to the network. The connection component 212 may be a transceiver for wireless connections and/or other signal processor for processing signals transmitted and received over a wired connection. Other medical devices (e.g., other dialysis machines) or components may be configured to connect to the network and communicate with the dialysis machine 200.

One or more heating elements 154 (FIG. 5B) may be disposed internal to the machine 200. For example, a cassette 224 may be insertable into an opening or cavity 210 (used interchangeably herein without the intent to limit) formed in the dialysis machine 200 in a direction indicated at arrow 214 as illustrated in FIG. 3 and into the heating chamber 152 positioned with the dialysis machine 200. In some embodiments, the cassette 224 may be configured so dialysate may continually flow through the cassette 224 to achieve a predetermined temperature before flowing into the patient. For example, in some embodiments the dialysate may continually flow through the cassette 224 at a rate of approximately 200 mL/min.

Figure 5A:
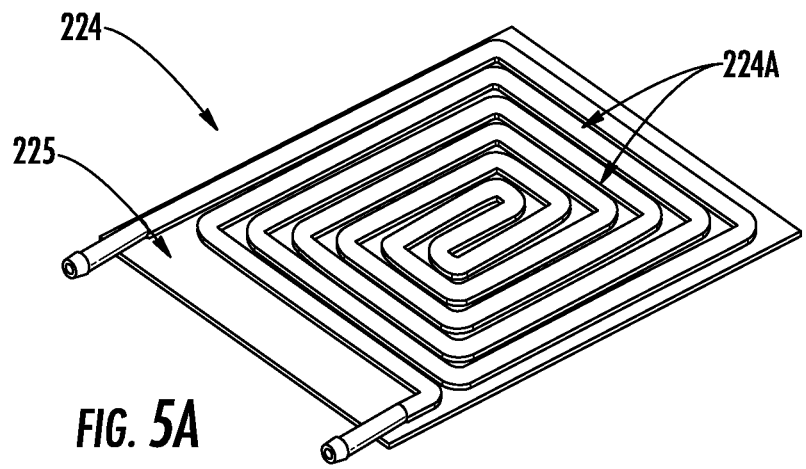
FIG. 5A illustrates a perspective view of a cassette that may be used in connection with the dialysis machine shown in FIGS. 3 and 4.
Figure 5B:
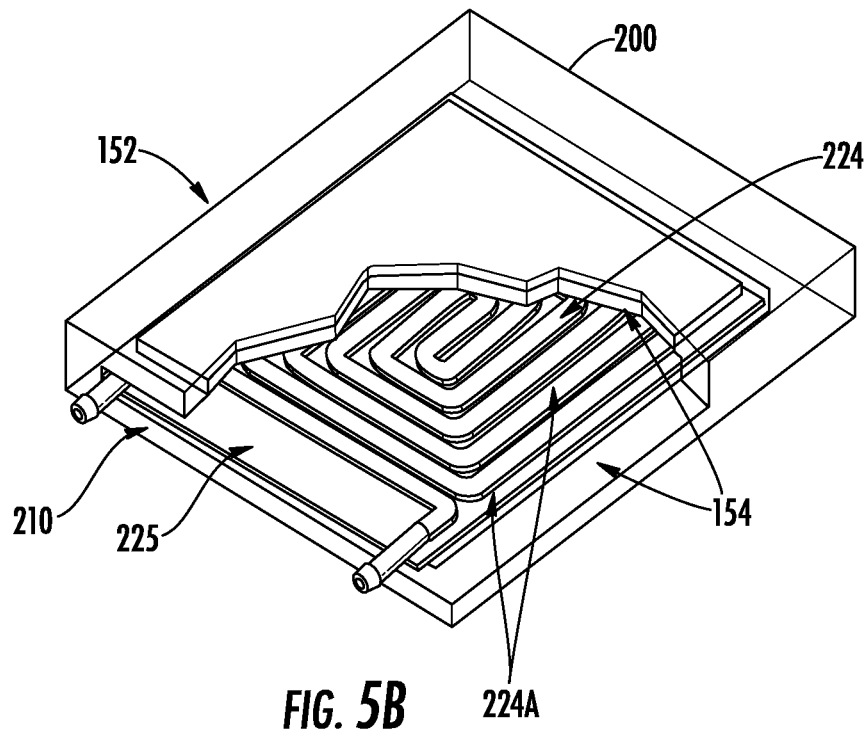
FIG. 5B illustrates a cut-away view of the cassette shown in FIG. 5A positioned within the heating chamber of the dialysis machine shown in FIGS. 3 and 4.

Referring to FIGS. 5A and 5B, the heating chamber 152 may include internal heating elements 154 positioned above and/or below the cavity 210, so that when the cassette 224 is inserted into the cavity 210, the one or more heating elements 154 may affect the temperature of dialysate flowing through the cassette 224. In some embodiments, the heating chamber 152 may be arranged and configured so that a portion of tubing in the system is passed by, around, or otherwise configured with respect to, one or more heating elements. In some embodiments, a dialysis machine 200 may provide an active measurement of the dialysate temperature in dialysate bags and/or a heating chamber, e.g., in the dialysate bags 122, and the heating chamber of FIGS. 1 and 3. It is understood that FIGS. 1 and 3 illustrate dialysate continuously flowing through the cassette 224 "in-line" with the dialysis machine 200, reaching an acceptable temperature by the application of internal heating elements.

In one embodiment, the cassette 224 may also include a filter (not shown). The filter may be any suitable filter such as, for example, a hydrophobic filter, so that air content may flow through the filter, but liquid such as the dialysate may be prevented by the filter from exiting the cassette. One example of an embodiment of a cassette and/or a filter is disclosed in U.S. Published Patent Application No. 2019/0076590 A1 to Plahey et al., entitled "Hydrophobic Filters for Air Management in Dialysis Machines," which is incorporated herein by reference in its entirety.

As previously mentioned, dialysate should be delivered to patients at specific temperatures, for example, at 37 degrees Celsius (e.g., body temperature). However, PD machines having in-line warmers may be susceptible to temperature variation of the dialysate. Additionally, as previously mentioned, it is desirable to heat the dialysate to the specified temperature as quickly as possible. Moreover, it would be advantageous to minimize the size of the cassette needed to heat the dialysate.

Referring to FIGS. 3-5B, PD machines 200 utilizing cassettes 224 and in-line heaters have been described. As shown in FIGS. 5A and 5B, the cassette 224 may include a housing 225 and a fluid flow channel 224A. The channel 224A may include a rectangular shaped profile for the dialysate to flow through, although alternate profiles are possible. In use, in one example of an embodiment, the cassette 224 is inserted into the heating chamber 152 with heating elements 154 located on top and bottom of the cassette 224, when properly positioned. Heat transfer from the heating elements 154 to the dialysate can be by conduction, convention, and/or radiation from the heating elements 154 to the outer surface of the walls of the channels 224A, conduction through the walls of the channel 224A, and conduction and convention from the inner surfaces of the walls of the channels into the dialysate.

As will be readily appreciated by one of ordinary skill in the art, the fluid flow through the channels 224A can be described as being laminar. Thus arranged, in laminar fluid flow, the existence of a boundary layer reduces heat transfer from the wall of the channels to the fluid. As such, heat transfer is rendered inefficient and more susceptible to temperature variation.

In accordance with one aspect of the present disclosure, heat transfer can be improved by changing fluid flow from laminar to turbulent. Thus arranged, heat transfer in turbulent flow is improved due to mixing of different fluid layers in the fluid flow, this is sometimes referred to as "eddy transport". By designing the channels 224A formed in the cassette 224 such that fluid flow of the dialysate is turbulent, improved (e.g., faster) heat transfer may be achieved thereby reducing the total treatment time. In addition, by designing the channels 224A formed in the cassette 224 such that fluid flow of the dialysate is turbulent, more efficient heat transfer may be achieved thereby reducing the overall size requirements of the cassette 224. In one example of an embodiment, it has been determined that the heat transfer rate in turbulent flow can be as much as 8× the heat transfer rate in laminar flow.

Figure 6:
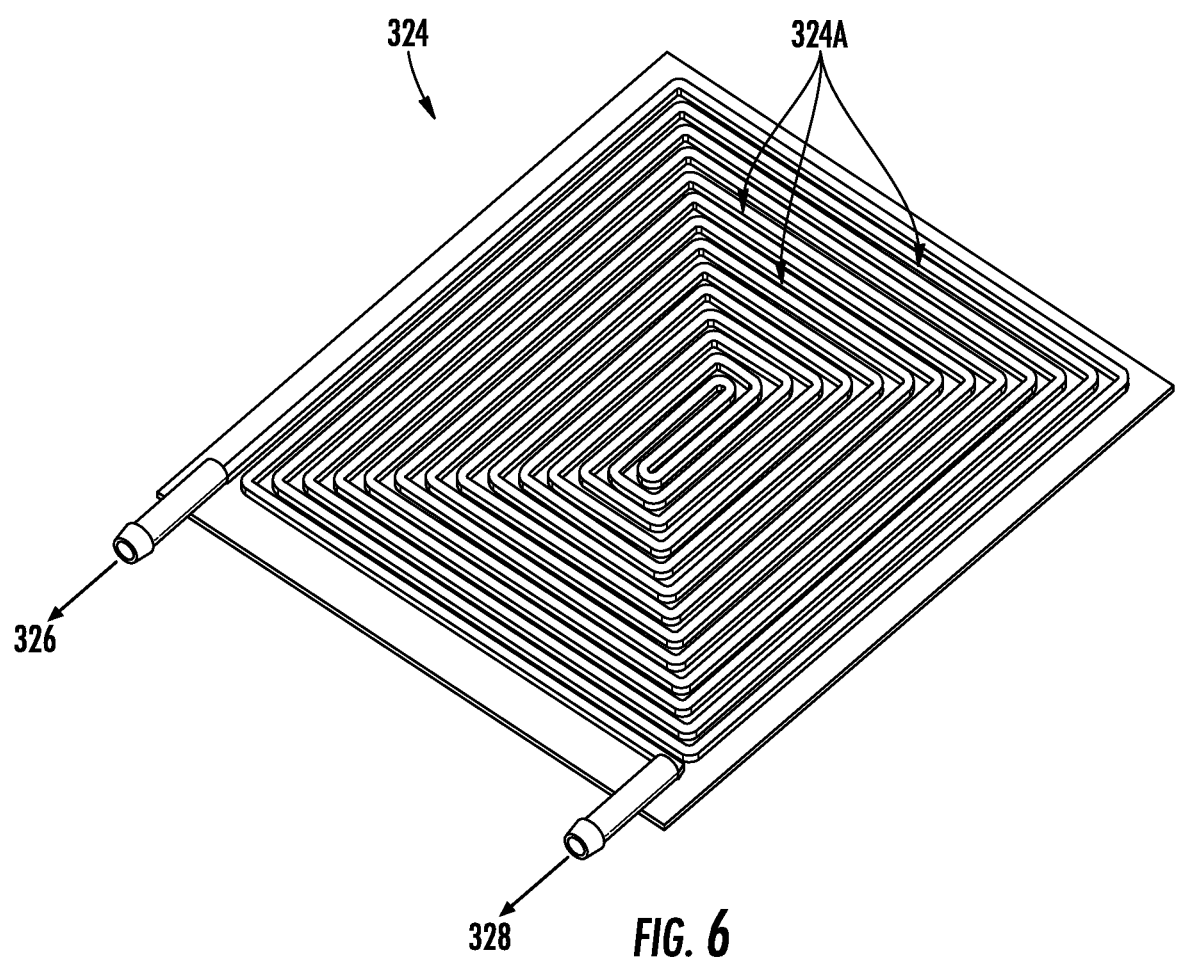
FIG. 6 illustrates an example of an embodiment of a cassette that can be used in combination with a dialysis machine in accordance with one aspect of the present disclosure.

In accordance with aspects of the present disclosure, turbulent flow can be arranged and configured in the channels of the cassette by any now known or hereafter developed mechanism. For example, in one example of an embodiment, referring to FIG. 6, the cassette 324, which may be used in place of cassette 224 shown in FIGS. 3-5B, may include channels 324A that are arranged and configured with a smaller cross-sectional area. That is, referring to FIG. 6, the cassette 324 may include an inlet 326 for receiving the fluid flow (e.g., dialysis) from a dialysis source (e.g., dialysis bag), a fluid flow channel 324A arranged and configured with a smaller, cross-sectional area, and an outlet 328 for delivering dialysis to the patient. By providing a decreased or smaller cross-sectional area for the channels (e.g., fluid flow path) formed in the cassette, turbulent flow may be achieved. That is, as will be appreciated by one of ordinary skill in the art, to determine whether fluid flow is laminar or turbulent, one typically calculates "Reynold's Number" ("Nr"), which is dependent upon several factors including velocity of the fluid, the cross-sectional area of the channel, and the kinematic viscosity of the fluid. Generally speaking, an Nr of less than 2,000 indicates a laminar flow while an Nr greater than 4,000 indicates turbulent flow. Cassettes utilizing in-line heating without turbulent flow may typically have an Nr of approximately 1,800 (e.g., typical fluid flow with a channel width of 6 mm and a height of 1 mm, and a velocity of approximately 300 ml/min). In accordance with one aspect of the present disclosure, by reducing the channel width, turbulent flow can be achieved. For example, in one example of an embodiment, by minimizing the channel width from 6 mm to 2 mm, Nr can be increased to approximately 4,200, ensuring turbulent flow. In various embodiments, the fluid flow channel is arranged and configured with a cross-sectional area of between 1.0 mm$^2$ and 2.1 mm$^2$. These dimensions are exemplary and other dimensions are envisioned. As will be appreciated by one of ordinary skill in the art, the cross-sectional area of the channel(s) may have any size and/or configuration now known or hereafter developed that causes the fluid flow to move in turbulent flow.

Figure 7:
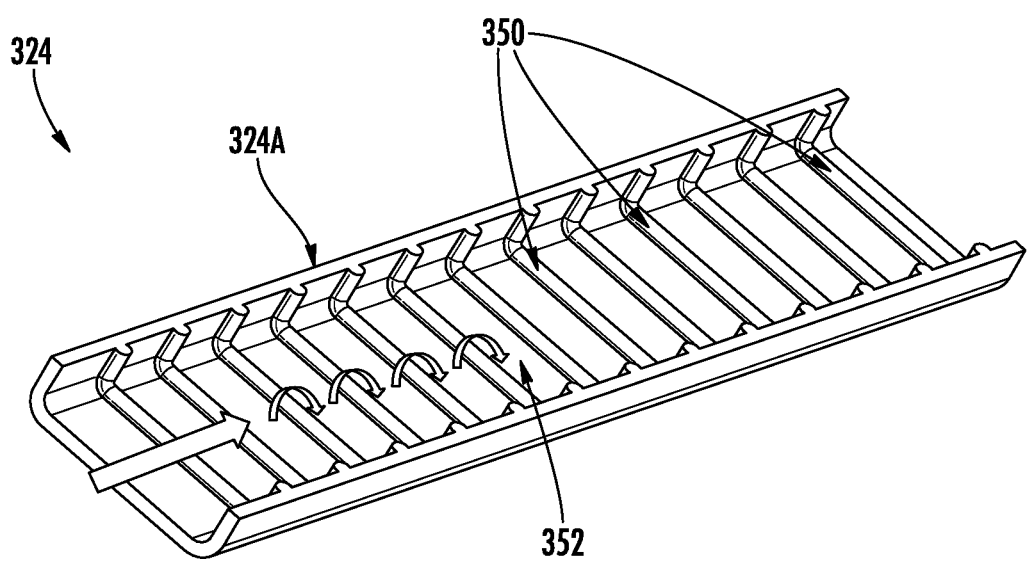
FIG. 7 illustrates a cut-away view of an example of an embodiment of a fluid flow channel of an alternate example of an embodiment of a cassette that can be used in combination with a dialysis machine in accordance with one aspect of the present disclosure.

In accordance with another aspect of the present disclosure, turbulent fluid flow in the channels of the cassette can be achieved by incorporating one or more projections, bumps, features, or the like (used interchangeably without the intent to limit) on an inner surface of the fluid flow channels. That is, referring to FIG. 7, the cassette 324, which may be used in place of cassette 224 shown in FIGS. 3-5B, may include one or more channels 324A that are arranged and configured with one or more projections or bumps 350 formed on an inner surface 352 of the channel 324A. In use, the projections or bumps 350 extend from the inner surface 352 of the channel 324A and protrude into the path of fluid flow to mix the fluid flow thus causing turbulent flow. In one example of an embodiment, the projections 350 may be formed in a flat sheet. Fluid flow channels 324A may then be created via, for example, heat sealing into the desired flow path. As will be appreciated by one of ordinary skill in the art, the projections 350 may have any size and/or configuration now known or hereafter developed that causes the fluid flow to mix resulting in turbulent flow.

Figure 8:
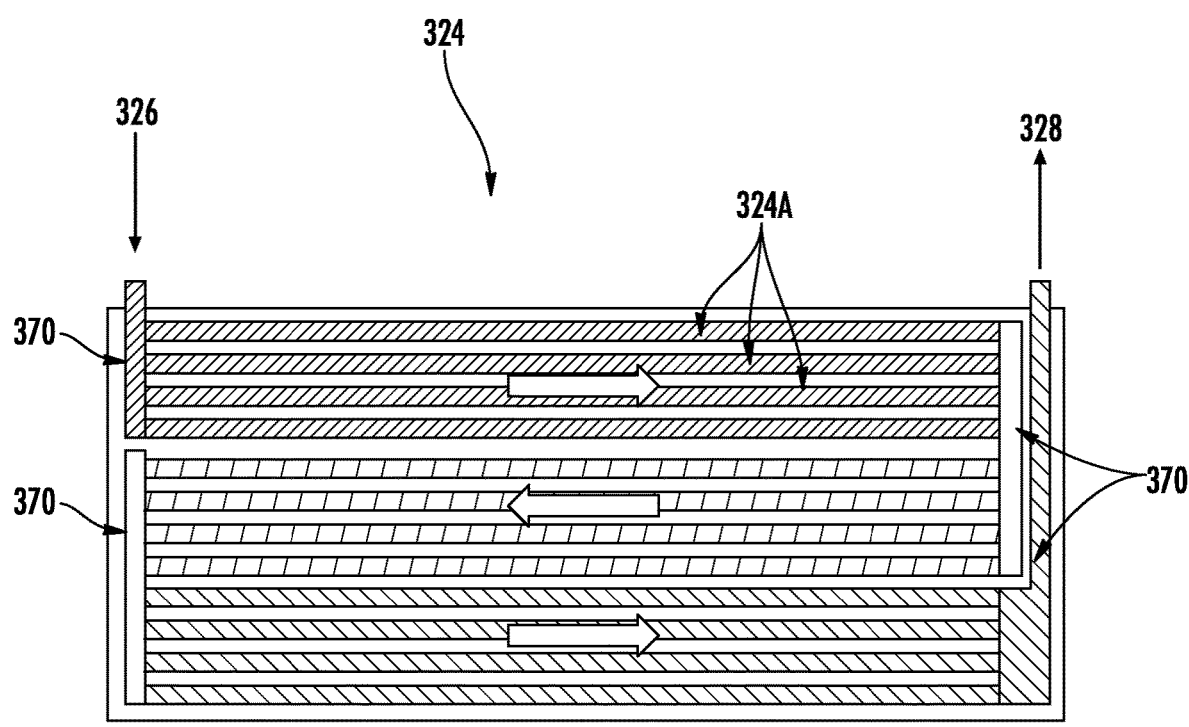
FIG. 8 illustrates an alternate example of an embodiment of a cassette that can be used in combination with a dialysis machine in accordance with one aspect of the present disclosure.

In accordance with another aspect of the present disclosure, which can be used independently or in combination with the other aspects of the present disclosure, parallel fluid flow paths may be provided. That is, referring to FIG. 8, the cassette 324, which may be used in place of cassette 224 shown in FIGS. 3-5B, may include an inlet 326 for receiving the fluid flow (e.g., dialysis) from a dialysis source (e.g., dialysis bag), one or more headers or junctions 370 to direct and subdivide the fluid flow into parallel channels 324A, and an outlet 328 for delivering dialysis to the patient. By providing one or more junctions or headers 370 to subdivide the fluid flow paths into multiple, parallel downstream channels 324A, smaller fluid flow pathways can be utilized, thereby increasing the efficiently of the heat transfer (e.g., the header subdivides a first or inlet pathway of the fluid flow channel into a plurality of downstream, parallel fluid flow pathways). In addition, dividing the fluid flow into multiple parallel channels will reduce the peak pressure needed to achieve the same flow rate.

Figure 9A:
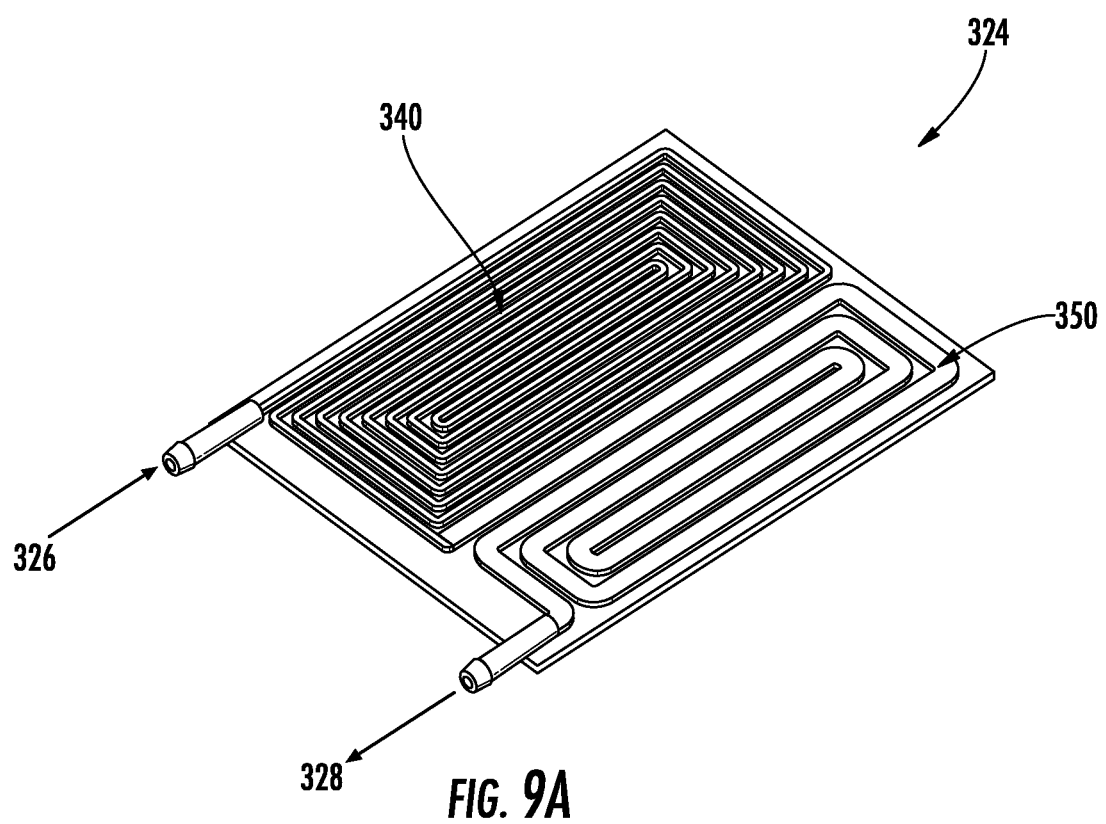
FIG. 9A illustrates a perspective view of an example of an embodiment of a cassette that can be used in combination with a dialysis machine in accordance with one aspect of the present disclosure.
Figure 9B:
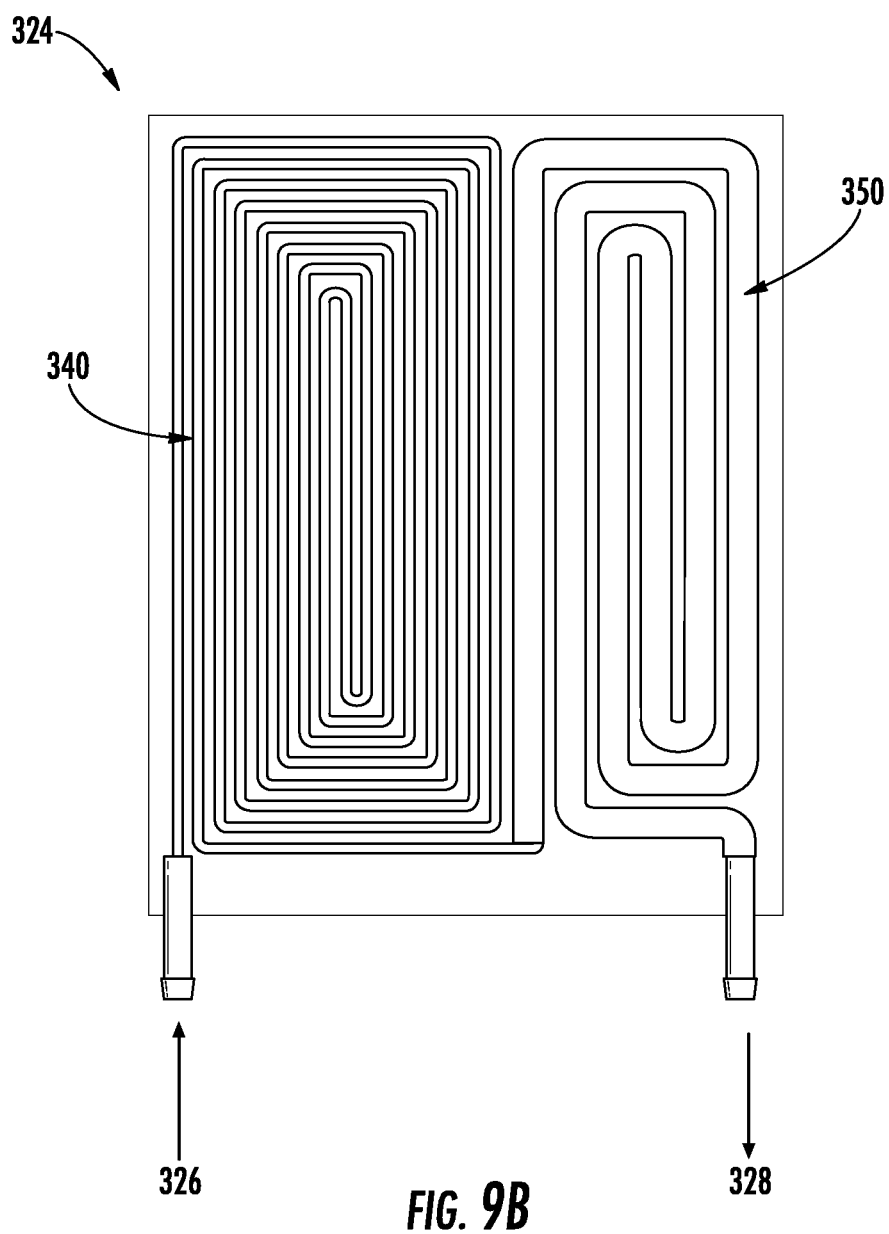
FIG. 9B illustrates a top view of the cassette shown in FIG. 9A.

Referring to FIGS. 9A and 9B, in accordance with one aspect of the present disclosure, an improved cassette 324, which may be used in place of cassette 224 shown in FIGS. 3-5B, may include multiple stages of fluid flow. As illustrated, the cassette 324 may include first and second stages of fluid flow 340, 350, although it is envisioned that more stages may be included. As shown, in use, the cassette 324 may include a first stage 340 of fluid flow where the channel is arranged and configured to provide turbulent fluid flow such as, for example, by incorporation of smaller cross-sectional area, incorporation of one or more projections, etc. The cassette 324 also includes a second stage 350 of fluid flow where the channel is arranged and configured to provide laminar fluid flow.

In the illustrated embodiment, the cassette 324 may include an inlet 326 for receiving dialysate from one or more dialysis sources (e.g., dialysis bags) 122 and an outlet 328 for enabling the dialysate to exit after it has been heated within the dialysis machine 200 (e.g., for delivering dialysis to the patient). Preferably, in one example of an embodiment, the first stage 340 of turbulent fluid flow is positioned adjacent to the inlet 326 so that the dialysate is initially passed through the heating chamber 152 via turbulent flow. Thus arranged, the dialysate may flow into the cassette 324 via the inlet 326 and into the heating chamber 152. Initially, the fluid flow may be through the first stage of turbulent fluid flow 340, then subsequently through the second stage of laminar flow 350, and then through the outlet 328 and eventually to the patient. By arranging and configuring the cassette 324 with first and second stages of fluid flow 340, 350, the dialysate may be initially subjected to faster heat transfer within the first stage of turbulent flow 340 to quickly heat the dialysate to a predetermined temperature such as, for example, a predetermined temperature just below body temperature. Thereafter, the heated dialysate may flow into the second stage of laminar flow 350 where the dialysate may be more accurately and finely tuned to its final temperature (e.g., body temperature). By combining the first and second stages (e.g., turbulent and laminar flow, respectively) in series, the benefits of quicker heat transfer provided by the first stage and better control provided by the second stage can be realized. In one example of an embodiment, the temperature of the dialysate could be continuously or intermittently monitored, sensed, etc. For example, the temperature of the dialysate could be monitored before entering the first stage of turbulent flow, before entering the second stage of laminar flow, and before entering the patient's body to more precisely and accurately deliver the dialysate at the desired temperature.

Figure 9C:
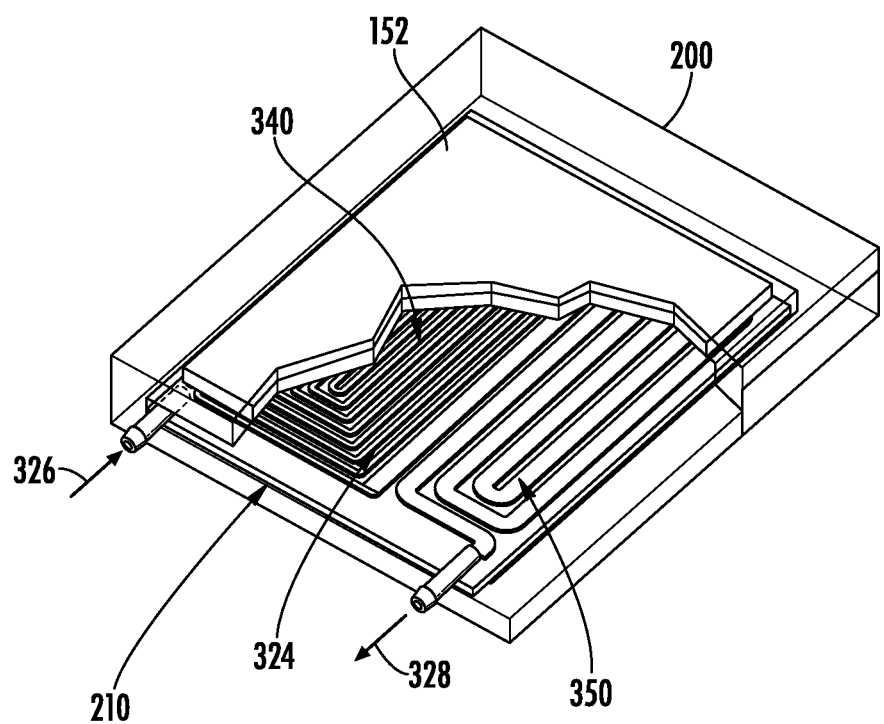
FIG. 9C illustrates a perspective, cut-away view of the cassette shown in FIG. 9A positioned within a heating chamber of a dialysis machine.
Figure 9D:
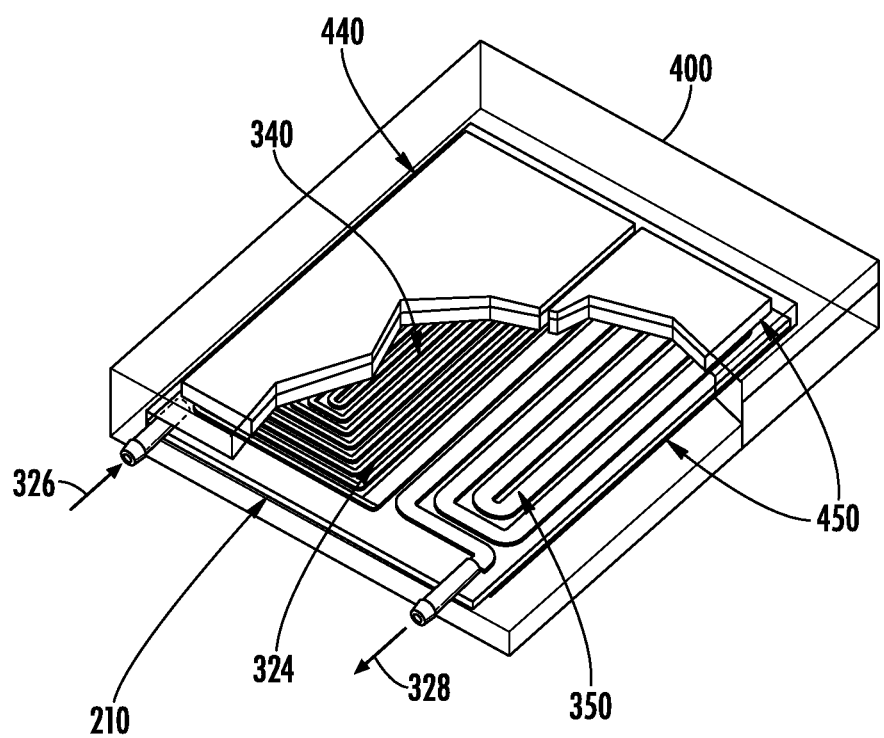
FIG. 9D illustrates a perspective, cut-away view of the cassette shown in FIG. 9A positioned within a heating chamber of a dialysis machine in accordance with another aspect of the present disclosure.

Referring to FIG. 9C, in use, the cassette 324 may be positioned within the heating chamber 152 of a dialysis machine 200. Alternatively, referring to FIG. 9D, in use, the cassette 324 may be positioned within the heating chamber of a dialysis machine 400 including first and second heating elements 440, 450 for heating the first and second stages of channel flow 340, 350, respectively. For example, in one embodiment, the second heating element 450 associated with the second stage of fluid flow 350 may be arranged and configured to operate at a lower temperature as compared to the first heating element 440 associated with the first stage of fluid flow 340. In this manner, more precise and accurate fine tuning of the dialysate temperature could be achieved. For example, in one embodiment, the first heating element 440 might be arranged and configured to operate at, for example, approximately 60° C. while the second heating element 450 might be arranged and configured to operate at, for example, approximately 45° C. In this manner, improved control over the final dialysate temperature can be provided.

Figure 10A:
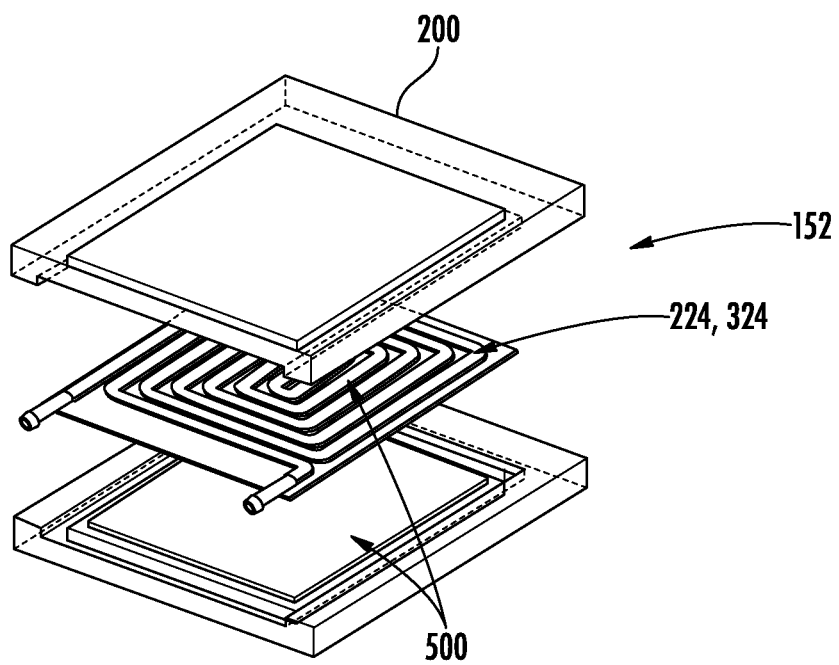
FIGS. 10A and 10B illustrate an example of an embodiment of a pouch for providing improved heat transfer in accordance with another aspect of the present disclosure.
Figure 10B:
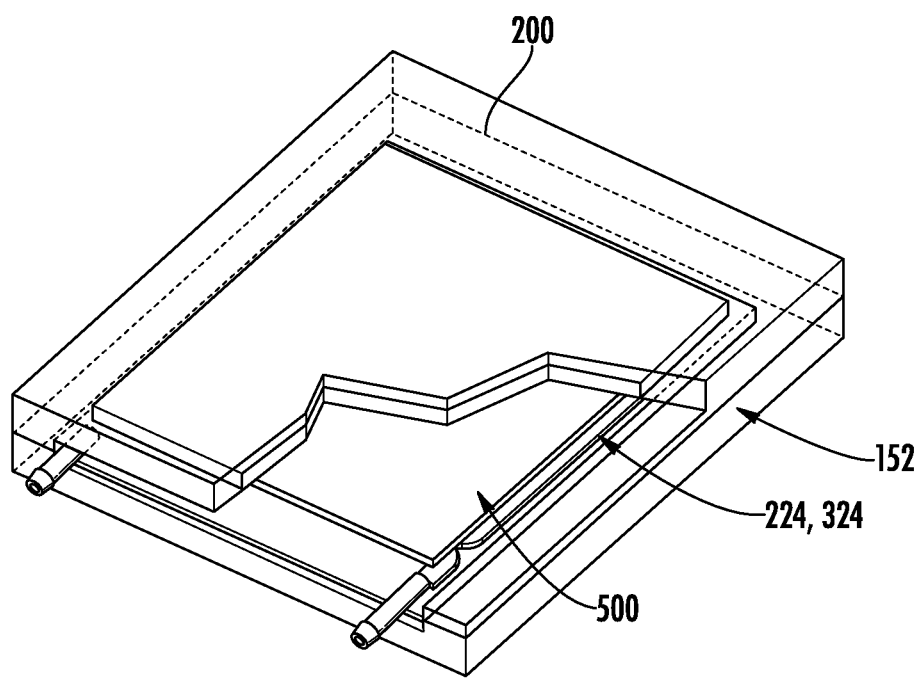

Referring to FIGS. 10A and 10B, in accordance with another aspect of the present disclosure, which can be used in combination with the other aspects disclosed herein, or singularly, an improved heating system is disclosed. That is, as shown, the heating system may include one or more pouches 500 for positioning between the heating elements 154 and the channels 224A, 324A formed in the cassette 224, 324 so that the pouches 500 are in contact with the heating elements 154 and the channels 224A, 324A formed in the cassette 224, 324. As shown, in one embodiment, pouches 500 may be positioned on either side of the cassette 224, 324 (e.g., a first pouch 500 may be positioned above the cassette 224, 324 between a top surface of the cassette and a heating element and a second pouch 500 may be positioned below the cassette 224, 324 between a bottom surface of the cassette and a heating element), although the incorporation of pouches are not limited to first and second pouches or any particular arrangement and/or configuration, and more or less pouches may be used in other embodiments. For example, it is envisioned a single pouch positioned above or below the cassette may be used.

In use, the pouches 500 can be manufactured from any suitable material now known or hereafter developed having good thermal conduction such as, for example, a gel pouch. Preferably, the gel pouch 500 includes sufficient compliance (e.g., very low modulus of elasticity) so as to maximize contact with the fluid flow channels formed in the cassette. Thus arranged, the gel pouch 500 facilitates improved distribution of heat transfer and the elimination, or at least minimization, of hot spots due to the geometry of the heating elements. In use, to ensure proper contact, the heating chamber should be opened when the cassette is being inserted (schematically illustrated in FIG. 10A) and then closed during use (schematically illustrated in FIG. 10B).

Various aspects described herein have been explained in connection with the dialysis machine 200 having a particular configuration. It is contemplated that the various aspects described herein may be used with dialysis machines having other configurations, for example, different types of dialysis machines and/or dialysis machines having cassettes positionable in other configurations and having other features, such as different types of pumps and/or dialysate heating systems. The system described herein may be used with any appropriate dialysis machine and/or other medical devices utilizing disposable cassettes that would benefit from improved in-line heating.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system for conducting a dialysis treatment, comprising:
   a dialysis machine for transferring dialysate to a patient from a dialysate source, the dialysis machine including a cavity and a heating chamber to heat the dialysate to a predetermined temperature; and
   a disposable cassette positionable within the cavity, the cassette being in fluid communication with the patient and the dialysate source, the cassette including a fluid flow channel;
   wherein the fluid flow channel is configured to cause turbulent flow of dialysate flowing through the fluid flow channel to provide increased heat transfer from the heating chamber to the dialysate,
   wherein the fluid flow channel includes a first stage and a second stage, the first stage of the fluid flow channel being configured to cause turbulent flow of dialysate flowing through the first stage of the fluid flow channel to provide increased heat transfer from the heating chamber to the dialysate, the second stage of the fluid flow channel configured to cause laminar flow of dialysate flowing through the second stage of the fluid flow channel.

2. The dialysis system of claim 1, wherein the first stage is configured to achieve a Reynold's Number (Nr) of 4,000 or greater.

3. The dialysis system of claim 1, wherein the first stage is configured with a cross-sectional area of between 1.0 mm$^2$ and 2.1 mm$^2$.

4. The dialysis system of claim 1, wherein the first stage has a width of approximately 2 mm and a height of approximately 1 mm.

5. The dialysis system of claim 1, wherein the first stage includes a plurality of projections extending from an inner surface thereof, the plurality of projections protruding into a path of the dialysate.

6. The dialysis system of claim 1, further comprising a header coupled to the fluid flow channel, the header subdividing a first pathway of the fluid flow channel into a plurality of downstream, parallel fluid flow pathways.

7. The dialysis system of claim 1, wherein the second stage of the fluid flow channel is in series with the first stage of the fluid flow channel.

8. The dialysis system of claim 7, wherein the fluid flow channel includes an inlet and an outlet, the first stage of the fluid flow channel being positioned in series between the inlet and the second stage of the fluid flow channel, the second stage of the fluid flow channel being positioned in series between the first stage of the fluid flow channel and the outlet.

9. The dialysis system of claim 7, wherein the heating chamber includes first and second heating elements for heating the first and second stages of fluid flow channel, respectively.

10. The dialysis system of claim 1, further comprising a thermal gel pouch positioned between a heating element of the heating chamber and the cassette, the pouch being in direct contact with the heating element and the cassette.

11. A disposable cassette positionable within a cavity of a dialysis machine that includes a heating chamber, the cassette being in fluid communication with a patient and a dialysate source for transferring dialysate therebetween, the disposable cassette comprising:

a fluid flow channel configured to cause turbulent flow of dialysate flowing through the fluid flow channel to provide increased heat transfer from the heating chamber to the dialysate, wherein the fluid flow channel includes a first stage and a second stage, the first stage of the fluid flow channel being configured to cause turbulent flow of dialysate flowing through the first stage of the fluid flow channel to provide increased heat transfer from the heating chamber to the dialysate, the second stage of the fluid flow channel configured to cause laminar flow of dialysate flowing through the second stage of the fluid flow channel.

12. The cassette of claim 11, wherein the first stage is configured to achieve a Reynold's Number (Nr) of 4,000 or greater.

13. The cassette of claim 11, wherein the first stage is configured with a cross-sectional area of between 1.0 mm$^2$ and 2.1 mm$^2$.

14. The cassette of claim 11, wherein the first stage has a width of approximately 2 mm and a height of approximately 1 mm.

15. The cassette of claim 11, wherein the first stage includes a plurality of projections extending from an inner surface thereof, the plurality of projections protruding into a path of the dialysate.

16. The cassette of claim 11, further comprising a header coupled to the fluid flow channel, the header subdividing a first pathway of the fluid flow channel into a plurality of downstream, parallel fluid flow pathways.

17. The cassette of claim 11, wherein the second stage of the fluid flow channel is in series with the first stage of the fluid flow channel.

18. The cassette of claim 11, wherein the fluid flow channel includes an inlet and an outlet, the first stage of the fluid flow channel being positioned in series between the inlet and the second stage of the fluid flow channel, the second stage of the fluid flow channel being positioned in series between the first stage of the fluid flow channel and the outlet.

19. The dialysis system of claim 1, wherein the fluid flow channel being configured to cause turbulent flow of dialysate flowing through the first stage of the fluid flow channel at a rate of about 200 mL/min.

20. The cassette of claim 11, wherein the fluid flow channel being configured to cause turbulent flow of dialysate flowing through the first stage of the fluid flow channel at a rate of about 200 mL/min.

* * * * *